United States Patent [19]

Mandl

[11] 4,148,306

[45] Apr. 10, 1979

[54] METHODS AND APPARATUS FOR TESTING AND MEASURING OF PSYCHOLOGICAL SUGGESTIBILITY COMPONENTS

[76] Inventor: Thomas H. Mandl, Oststrasse 20, 4005 Meerbusch 1, Fed. Rep. of Germany

[21] Appl. No.: 810,809

[22] Filed: Jun. 28, 1977

[30] Foreign Application Priority Data

Jun. 30, 1976 [DE] Fed. Rep. of Germany ....... 2629361

[51] Int. Cl.² ............................................. A61B 5/16
[52] U.S. Cl. .................................... 128/2 N; 35/22 R
[58] Field of Search ....................... 128/2 N, 2 S, 2 R; 35/22 R

[56] References Cited

U.S. PATENT DOCUMENTS

| 2,685,286 | 8/1954 | Torricelli | 128/2 N |
| 3,477,422 | 11/1969 | Jurist, Jr. et al. | 128/2 R |

FOREIGN PATENT DOCUMENTS 1002866 9/1965 United Kingdom ..................... 128/2 N

*Primary Examiner*—Lee S. Cohen
*Attorney, Agent, or Firm*—Van Metre Lund

[57] ABSTRACT

A system is provided for measuring psychological suggestibility components in which certain physical stimuli are applied to a subject's arm or other body part and the subject's reaction is detected. The arm is supported by three parallel bar members, the intermediate member being stationary and the two outside members being moved downwardly to suggest to the subject a downward movement of his arm. In addition, squeezing forces are applied through a flexible and stretchable element extending from one of the outside members over the arm to the other of the outside members. Also, pointed prongs are movable downwardly against the upper surface of the subject's arm to apply uncomfortable pressure thereto. The vertical position of the subject's arm and vertical movement thereof are indicated by lights energized from contact devices associated with certain of the prongs. A cover extends over the subject's arm to shield the mechanism from view and an arrangement is provided in the back of a chair in which the subject sits during testing. A variety of tests may be performed by a lay person according to prescribed procedures with objective results which are independent of any personal relationship between the subject and the person conducting the tests.

15 Claims, 8 Drawing Figures

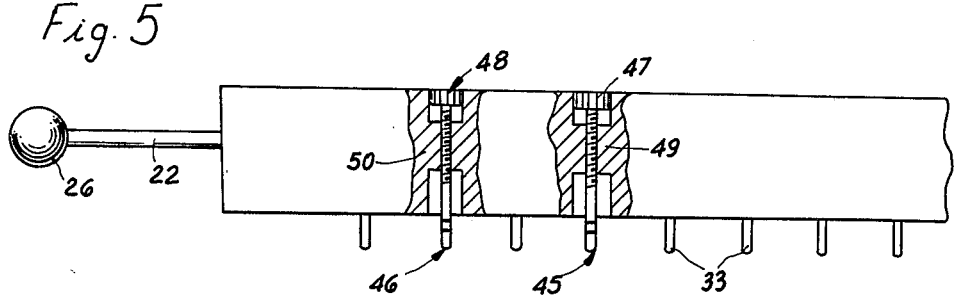
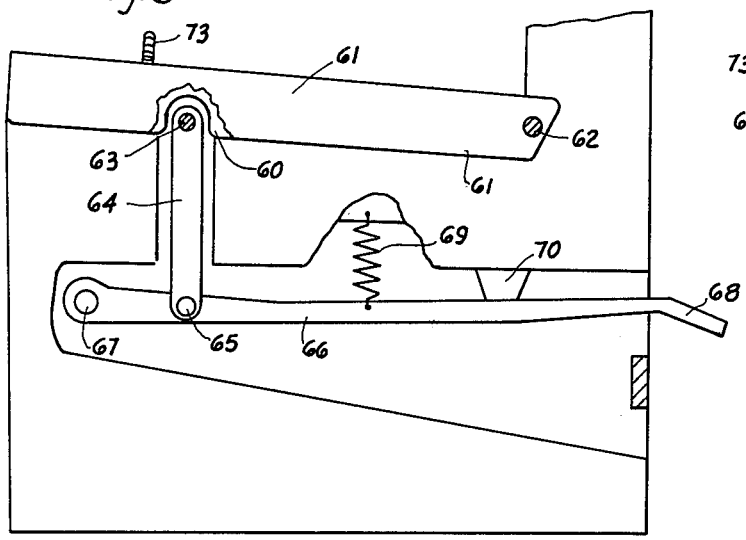
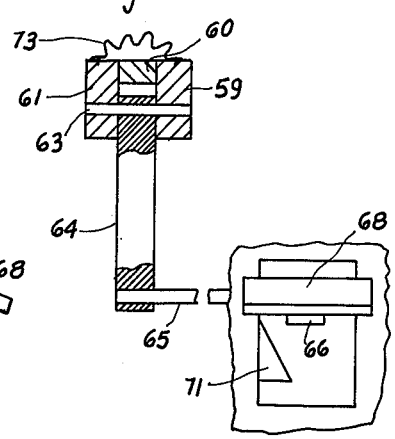
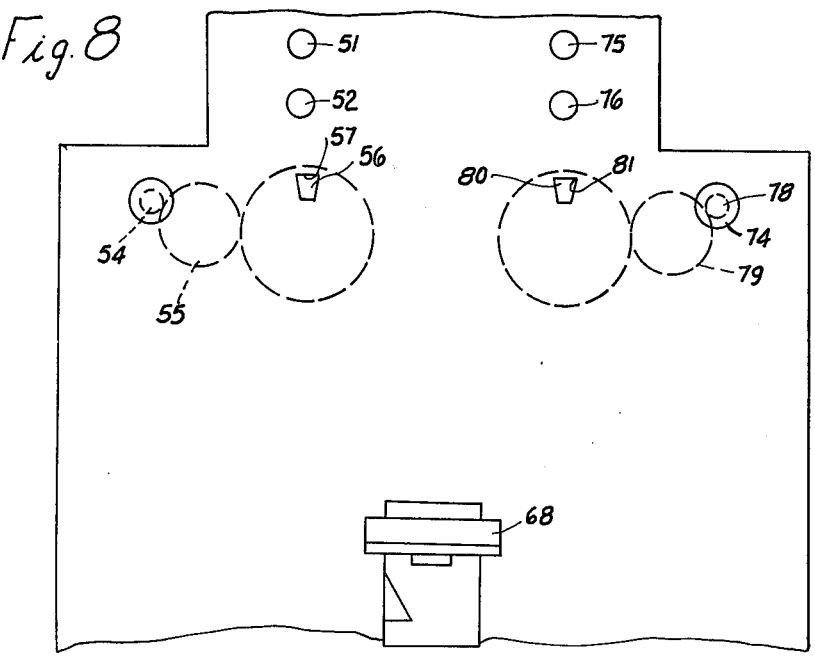

METHODS AND APPARATUS FOR TESTING AND MEASURING OF PSYCHOLOGICAL SUGGESTIBILITY COMPONENTS

This invention relates to methods and apparatus for testing and measurement of psychological suggestibility components and more particularly to methods and apparatus by which such components can be accurately and reliably measured with a high degree of objectivity. The tests can be conducted by a lay person according to prescribed procedures and results are obtained which are substantially independent of any personal relationship between the subject and the person conducting the test.

BACKGROUND OF THE PRIOR ART

Many psychological tests have heretofore been used or proposed for measuring components of a subject's behavior. Such tests may be divided into three general groups.

A first group of tests includes psychometric tests such as intelligence tests, for example, which are highly structural with the problem and the result being very clear and with the answers being either right or wrong. Such tests may be administered by lay persons but have little application to testing of components of a psychological nature.

A second group of tests includes projection tests which have been used in measuring psychological components. Such tests are not highly structural and the solutions are many-fold with neither right nor wrong answers which depend upon the analysis of the subject by the person administering the test. Such tests involve insight into the subject's mind and require a qualified psychologist to administer the test.

A third group of tests includes "objective" tests in which the aim or result of the test is totally unknown to the subject. In such tests as conducted in the prior art, there is a premise which is empirically verifiable and whose theoretical basis need not be known. For instance, a correlation between darkness and a proneness toward neuroses, a correlation between acceleration of pulse rate and anxiety and a correlation between intellectual work and muscle tension may be assumed. In such tests, an attempt is made to create a test situation which is as close as possible to a real-life situation on the assumption that the subject's reaction or behavior is closely related to his general functioning. Such an assumption is questionable and objective tests are not refined enough to be useful for diagnostic purposes.

In spite of the huge number of known psychological tests, there has been no known theoretical or practical measurement of suggestion or suggestibility which has been considered a nebulous factor or component. Attempts may be made in known types of tests to recreate the same reaction obtained previously in an analagous situation, but it is questionable whether in such tests, a given result is due to a suggestibility factor or due to a learning process performed during the test.

There is such a thing as a so-called "prestige suggestion" involving thought and feeling processes. For example, so-called body sway tests have been performed in which to a blind-folded person or to one in a dark room, a command is made "Attention, you are falling forward," and most subjects will lean forward in response. Such tests as heretofore been made have been of very limited value because they are limited to verbal instructions which cannot be modified and are inexact because it is difficult to qualify or quantify the relationship between the person conducting the test and the subject being tested. The same subject might respond to a command given by one testing person and not respond to the same command given by a different testing person.

SUMMARY OF THE INVENTION

This invention was evolved with the general object of overcoming the disadvantages and inadequacies of prior testing systems and of providing a system in which factors or components of suggestibility are taken into account and accurately and reliably measured while obtaining a level of objectivity such that the person administering the test may be a lay person. Certain specific objects of the invention relate to providing test methods for measuring suggestibility components and components related thereto and other specific objects relate to the provision of apparatus with which such methods can be readily and expeditiously performed in a highly reliable and objective manner.

In accordance with the invention, a part of a subject's body is so placed as to permit detection and measurement of the subject's reaction to a suggestive stimulus while the subject is unaware of the purpose of the test and of the meaning of any reaction thereto. Preferably, at least one suggestive stimulus is physically applied to the same body part where the reaction is detected, with the subject being also unaware of the actual nature of the suggestive stimulus.

In accordance with a specific feature of the invention, a movable part of a subject's body, such as his arm, is placed in a support which is covered and which includes a plurality of support surfaces engaged by adjacent portions of the movable body part. Then at least one of such support surfaces is moved downwardly while at least one of the others is stationary suggesting to the subject that support of his arm is being withdrawn. Simultaneously, another physical stimulus may be applied, such as a squeezing force on the arm and in addition, a slightly painful or uncomfortable pressure may be applied.

The reaction of the subject is measured as by detecting whether the subject moves his arm upwardly or otherwise reacts in response to the stimulus or stimuli. A verbal reaction may be significant and may be recorded. Also, the time between the application of the stimulus or stimuli and reactions produced, is any, are measured and recorded.

The system constitutes the synthesis of the three basic types of tests set forth hereinabove. The stimuli can be highly structured, variable and modifiable to obtain the advantages of psychometric tests but does not have the limitations of such tests. The reactions of the subjects are limited and clear answers are obtained to obviate the nebulous types of results obtained by projection tests. The tests are independent of any relationship between the person performing the test and the subject being tested and can be performed by lay persons. At the same time, the results cannot be distorted by the subject because both the aim of the test and the nature of the stimuli applied are unknown to him.

With proper programming of the tests, results are obtained which are useful for diagnostic purposes and also for prognostic purposes. The tests can be used in measuring general aptitudes and for career counselling, for example, in evaluating the subject's aptitude for professions in which dealing with people is important and with the suggestibility component of a subject's behavior is correspondingly important.

It is extremely important that the test can be administered and analyzed in a manner such that they are totally independent of any personal relationship between the person administering the test and the test subject.

With proper structuring of the tests of the invention, they are usable for measuring abilities which are desirably possessed by persons in positions of leadership, such as abilities to act independently in relation to stimuli rather than by suggestion. The tests can measure paradoxical reactions and are also valuable for diagnostic purposes and choice of specific treatments.

In addition to or instead of applying a stimulus by mechanical means, a stimulus can be initiated acoustically and, if desired, by carefully prescribed verbal instructions.

Specific features of the invention relate to the construction of the device for performing the tests. The support arrangement preferably includes three supports in the form of parallel bars with means to lower at least one of the bars. Preferably, the middle bar is stationary while the outer two bars may be controllably lowered. Pain-creating means are provided, preferably in the form of a plurality of rows of pointed prongs which may be lightly engaged with the upper surface of the arm or other bodily part. To detect physical reaction, means are provided for sensing physical movement of the body part, preferably including electrical contact devices connected to suitable indicating lamps.

This invention contemplates other objects, features and advantages which will become more fully apparent from the following detailed description taken in conjunction with the accompanying drawings.

BRIEF DESCRIPTION OF THE DRAWINGS

FIG. 5 is a view illustrating certain electrical contact devices and also illustrating the relationship of mechanism to the arm of the subject of a test;

FIG. 6 is an elevational view illustrating elements of the mechanism used for controlling vertical movement of certain arm support bar members;

FIG. 7 is a rear elevational view showing the mechanism of FIG. 6; and

FIG. 8 is a rear elevational view of the chair illustrating indicating and control means of the apparatus.

DESCRIPTION OF A PREFERRED EMBODIMENT

Figure 1:
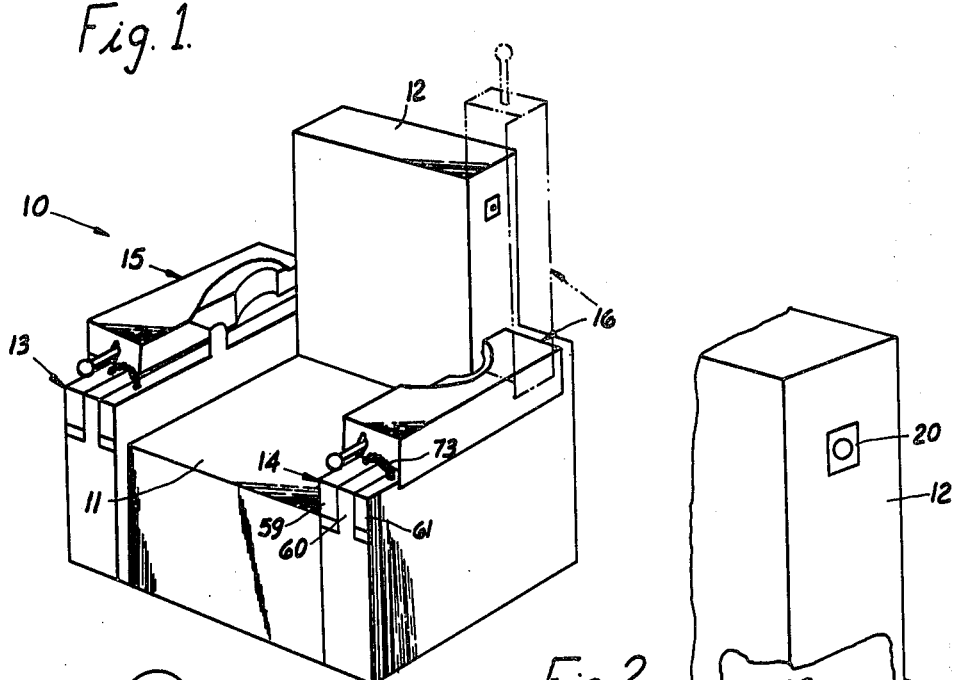
FIG. 1 is a perspective view of a test chair which incorporates testing mechanism constructed in accordance with the invention.

Reference numeral 10 generally designates a test chair incorporating apparatus for measurement of psychological suggestibility components in accordance with the principles of this invention. In general, the chair 10 includes a seat 11, a back 12 and two arm rest structures 13 and 14 with which mechanisms of the invention are associated, operative to apply certain physical stimuli to a subject's arms and to measure physical reactions of the subject thereto. The mechanisms which are associated with the arm rest structures 13 and 14 include elements which are carried under cover structures 15 and 16 which are pivotal on a common horizontal axis near the rear of the arm rest structures 13 and 14, for movement between upright inoperative positions as illustrated in broken lines and operative positions over the arms of the subject, as illustrated in full lines in FIG. 1.

Figures 2, 3:
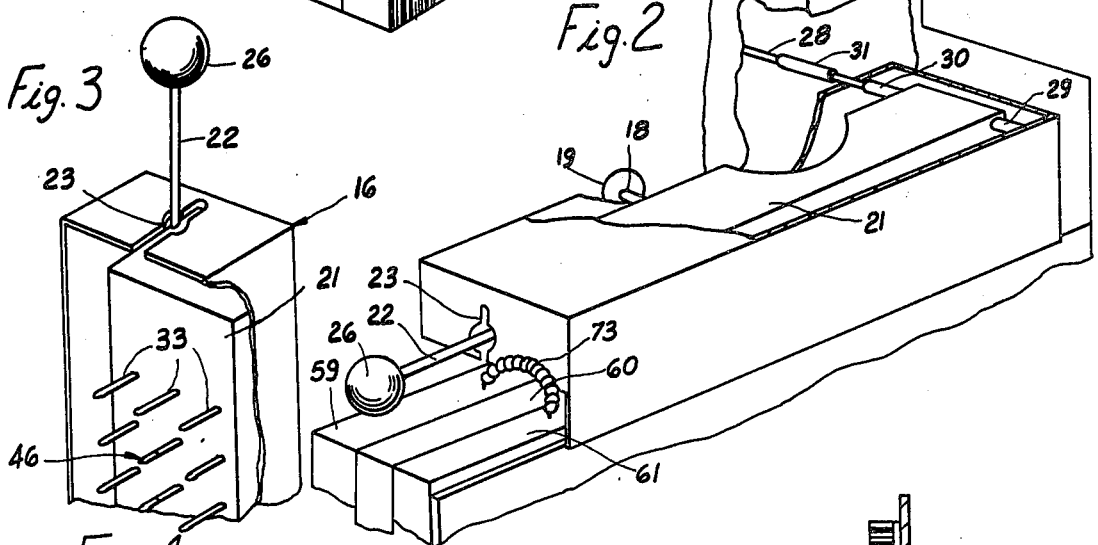
FIG. 2 is a view illustrating a part of the chair including one arm thereof, on an enlarged scale, certain parts being broken away to show the construction of the mechanism.
FIG. 3 is another perspective view of a portion of the mechanism in an alternate inoperative position, illustrating further details of construction.
Figure 4:
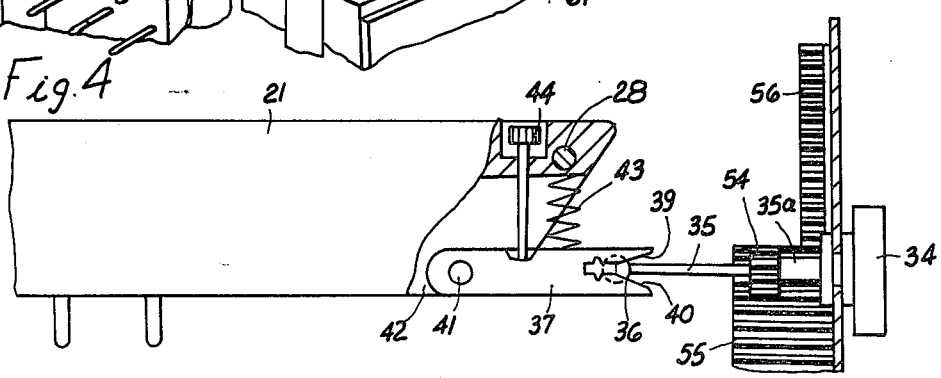
FIG. 4 is a elevational view showing a rearward portion of a test mechanism and its connection to control means in the back portion of the chair.

FIG. 2 illustrates portions of the mechanism associated with the arm rest structure 14 and cover 16, it being understood that the mechanisms associated with the arm rest structure 13 and cover structure 15 have a similar construction. The cover structure 16 carries a ball detent element 18 for releasable locking engagement with a recess in an element 19 upstanding from the arm rest structure 14 and an element 20 which is carried at the side of the upper portion of the back 12 of the chair. A board 21 is disposed within the cover structure 16 and a rod 22 connected thereto extends through a slot 23 in a forward wall portion of the cover structure 16. The slot 23 may be provided with resilient means (not shown) for frictional engagement with the rod 22 and preferably has a central widened portion as illustrated. A knob 26 is shown secured to the forward end of the rod 22.

Both the cover structure 16 and the board 21 are supported for pivotal movement about a common horizontal axis. A shaft 28 secured to the board 21 extends through sleeves 29 and 30 which are carried by the cover structure 16 and also extends through a fixed sleeve bearing 31 carried within the back 12 of the chair 10.

The board 21 carries a plurality of depending prongs 33 for engagement with the upper surface of the subject's arm, preferably arranged in three rows with ten prongs in each row. When the cover structure 16 and prong-carrying board 21 are in the operative position, the angular position of the board 21 is adjustable by rotation of a knob 34 at the rear of the chair, to control the pressure of engagement between the prongs 33 and the arm of the subject. The knob 34 is affixed on the end of a shaft 35 which extends through a support bearing 35a and which carries at its forward end an element 36 which has frusto-conical surface portions arranged for releasable locking engagement with recesses in the rearward end of a lever 37, the lever 37 having converging surfaces 39 and 40 defining an entrance opening, facilitating entry of the element 36 into locking engagement in the rearward end portion of the lever 37.

The lever 37 is adjustably carried from the prong-carrying board 21. In particular, the forward end of the lever 37 is pivotally supported through a shaft 41 carried by a bracket 42 which is affixed to the board 21. A tension spring 43 is connected between a rearward end portion of the lever 37 and the axle shaft 28 and an adjustment screw 44 is threaded through a portion of the bracket 42 to engage an intermediate portion of the lever 37. Thus by adjustment of screw 44 the vertical position of the rearward end portion of the lever 37 may be adjusted to facilitate alignment with the element 36, and to facilitate locking engagement therewith. The rod 35 is held against axial movement and the forward end thereof is threaded through the element 36 so that upon rotation of the knob 34, the prong-carrying board 21 is rotated about the axis of the shaft 28, to control the pressure of engagement between the prongs 33 and the arm of the subject.

Means are provided for indicating the pressure between the prongs and the subject's arm and also for sensing movement of the subject's arm. In particular, two contact switch devices 45 and 46 are substituted for two of the prongs, preferably in the middle row. The construction of such devices 45 and 46 is not illustrated in detail but each has a resiliently supported end portion and each includes a contact which is closed when a predetermined pressure is applied to the end portion thereof. The device 45 and 46 are mounted on the ends of screws 47 and 48 which are threaded through portions 49 and 50 of the prong-carrying board 21.

Devices 45 and 46 are respectively connected to indicating lamps 51 and 52 which may preferably be mounted in the rear face of the chair back 12. In operation, after swinging the board 21 together with the cover structure 16 downwardly to an operative position over a subject's arm and after obtaining a locked interengagement between the rearward end of the lever 37 and the element 36, the knob 34 may be rotated to a position just beyond that at which the lamp 51 flickers, indicating a certain pressure engagement between the device 45 and the subject's arm. The position of the device 46 is so adjusted that at this time, the lamp 52 will not be energized, but such that upon a predetermined upward movement of the person's arm, the switch device 46 will be operated to a closed position to energize the lamp 52. Thus lamp 51 is used in initially adjusting to a reference level while lamp 52 indicates a predetermined movement of the subject's arm above such a reference level.

Means are also provided for indicating the angular position of the knob 34 and for permitting adjustment to obtain a predetermined pressure engagement with the subject's arm. In particular, as diagrammatically illustrated in FIG. 8, the shaft 35 carries a gear 54 which is meshed with a gear 55 and which is meshed in turn with a gear 56, the gear 56 preferably having indicia on the rearward face thereof visible through an opening in the rearward wall of the chair back 12 to indicate the angular position of the gear 56 and to thus indicate the angular position of the knob 34 and the prong-carrying board 21. After adjusting the knob 34 to a position just beyond that at which the lamp 51 flickers, the position of the gear 56 as indicated through the opening 57 may be noted and recorded. Then, in testing operations in which it is desired to apply a predetermined additional pressure to the subject's arm through the prongs, the knob 34 may be rotated to rotate the gear 56 through a predetermined angle from the initial position.

Referring to FIGS. 2, 6 and 7, the arm rest structure 14 includes three parallel bars 59, 60 and 61, bar 60 being stationary and being disposed between bars 59 and 61. The bars 59 and 61 are rigidly secured at their rearward ends to a shaft 62 which is journalled in the rearward portion of the chair for rotation about a horizontal axis. Bars 59 and 61, at an intermediate point, are also connected through a pin 63 to the upper end of a link 64 which has a lower end connected to one end of a shaft 65, the opposite end of which is connected to a link of a mechanism for the opposite arm, similar to the link 64. At an intermediate point, shaft 65 is carried by an intermediate portion of a lever 66 which has a forward end pivotally supported on a shaft 67 and which has a rearward end in the form of a pedal 68, projecting rearwardly from the chair back 12. A tension spring 69 is provided between lever 66 and a fixed portion of the chair to engage the lever 66 with a fixed stop 70. When the lever 66 is moved downwardly by engagement of the pedal 68, beyond a certain position, it may be releasably locked in a downward position by a latch device 71 which is suitably releasable to permit return movement of the lever 66.

When lever 66 is engaged with the fixed stop 70, the upper surfaces of the bars 59 and 61 are flush with the upper surface of the stationary bar 60. Then when the lever 66 is moved downwardly, the bars 59 and 61 are moved downwardly to suggest to the subject an upward movement of his arm, to which he may or may not react. Preferably, a flexible covering of a stretchable cloth or the like may extend from bar 59 to bar 61 over the bar 60 so that in the rest position, the fact that there are three sets of bars is not visible to the subject.

A stretchable and flexible element such as a coiled spring 73 is provided which may be covered if desired and which is connected between the movable bars 59 and 61. The spring 73 is looped over the wrist of the subject when his arm is placed on the support 14 and, when the movable bars 59 and 61 are moved downwardly through operation of the lever 66, a squeezing force is applied to the wrist of the subject.

As above indicated, the arm rest structure 13 and the cover structure 15 on the opposite side of the chair may have mechanisms associated therewith which are like those described above and as shown in FIG. 8, a knob 74 may be provided corresponding to knob 34, lamps 75 and 76 may be provided corresponding to lamps 51 and 52, and gears 78, 79 and 80 may be provided corresponding to gears 54, 55 and 56 with the gear 80 having indicia visible through an opening 81 corresponding to the opening 57. It will be noted that the operating knobs 54 and 74 and the operating pedal 68 are on the back of the chair and likewise the indicating elements 51, 52, 57, 75, 76 and 81 are all on the back of the chair, not visible to the subject of the test.

A number of different types of tests may be performed with the chair 10 as illustrated and described. In one type of test, prescribed explanations and instructions may be given to the subject to minimize any anxiety which he may have and to prevent the subject from over-reacting to any stimulus applied to him. In general, the explanations given to the subject should be such that he will be unaware of the purpose of the tests and rather than avoiding any comment as to the purpose of the tests, the subject may be purposely misled as by telling him that the test is part of a physical examination. If desired, a helmet might be placed on the subject to give him the impression that brain waves are being measured and influenced. Correct, but incomplete, information may be given as to the construction and operation of the mechanism. The subject may be told, for example that the mechanism includes prongs which will exert pressure on his arm and may cause a slight discomfort but which will not be injurious. Explanations and instructions should be simple and concise and should be such that they should be given by a lay person to be the same from one subject to another.

With the subject sitting in the test chair 10, his hands are inserted through the spring element 73 and a corresponding element on the opposite side with his forearm being placed on the supports 59, 60 and 61 which are preferably covered by a flexible cloth as above indicated and which are flush with each other. Then the cover structures 15 and 16 are moved downwardly to the illustrated positions and the knobs 34 and 74 are adjusted to points just beyond that at which the lamps 51 and 75 flicker.

The subject may be told, in one type of test that the mechanism will operate to lift his arm and after he is positioned in the chair, a humming tone may be initiated while the pedal 68 is slowly depressed and, at the same time, the subject may be told that a current is being applied to raise his arm. The following subjective and objective reactions are possible.

1. Reaction-objective-positive (ROP) The subject may actually raise his arm or arms to cause energization of lamps 51, 75.

2. Reaction-subjective-positive (RSP) The subject without raising his arms may say that he has done so.

3. Reaction-objective-negative (RON) The subject may not raise his arms.

4. Reaction-subjective-negative (RSN) The subject may say that he has not raised his arm; may simply say nothing.

The following four combinations of such reactions are possible:

1. ROP and RSP, wherein the subject actually raises his arms and says he has done so indicates that he is either subject to suggestions or that he has a cooperative attitude or both.

2. RON and RSN, wherein the subject does not actually raise his arms and says that he has done so, indicating that he is not subject to suggestion but that he likes to cooperate.

3. ROP and RSN, wherein the subject actually raises his arm and says nothing which indicates that he is subject to suggestion, but is not necessarily cooperative.

4. RON and RSP, wherein the indication is that the subject may be subject to the suggestion. This discrepancy, like other discrepancies, may be of diagnostic significance.

In other types of tests, the subject may be given no instructions other than those intended to put him at ease while not letting him know the purpose of the testing procedure. The great variety of such possible tests are not described but it is noted that through the operation of the indicating lamps 51, 52, 75 and 76, the operation of the knobs 54 and 74 and the indication of the angular positions thereof through the openings 57 and 81 and through the operation of the pedal 68, the operations can be accurately controlled and reproduced in substantially identical fashion from one subject to another. His reactions as indicated from the indicating lamps and also his verbal reactions may be carefully recorded together with elapsed times between the application of stimuli and his reactions thereto.

It will be understood that modifications and variations may be effected without departing from the spirit and scope of the novel concepts of this invention.

I claim as my invention:

1. In apparatus for measuring a subject's psychological suggestibility component, support means for supporting a part of a subject's body, stimulus means associated with said support means for administerinng a certain physical stimulus to said body part such as to produce a reaction in proportion to the subject's psychological suggestibility component, and detection means associated with said support means for detecting when said reaction exceeds a certain threshold value.

2. In apparatus as defined in claim 1, said support means including a plurality of members having upper surfaces for supporting adjacent portions of said body part, at least one of said members being stationary, and said stimulus means including means for lowering at least one of said members to suggest lowering of said body part to the subject.

3. In apparatus as defined in claim 2, said detection means including means for detecting a raising movement of said body part.

4. In apparatus as defined in claim 3, cover means for extending over said body part during support thereof on said support means to preclude the subject's visual observation of the body part and its support and movements.

5. In apparatus as defined in claim 4, said means for detecting a raising movement of said body part including electrical contact means supported from said cover means and arranged to sense upward movement of said body part, and indicating means controlled from said electrical contact means.

6. In apparatus as defined in claim 5, said electrical contact means including first and second contact devices for measuring pressure at adjacent portions of the surface of the body part said indicating means including first and second indicating means associated with said first and second contact devices, means for adjusting the vertical position of said electrical contact means to a position such as to cause operation of said first indicating means while said body part is in a rest position resting on said support means, and said second indicating means being operated from said second contact device when the body part is moved upwardly from said rest position.

7. In apparatus as defined in claim 1, said stimulus means comprising pressure means for applying a slightly uncomfortable pressure against the surface of said body part.

8. In apparatus as defined in claim 7, said pressure means comprising a structure adopted to extend over said body part, a plurality of prongs depending from said structure for engaging the upper side of said body part, and means for moving said structure downwardly to increase the pressure between the lower ends of said prongs and the surface of the body part.

9. In apparatus as defined in claim 1, said stimulus means comprising squeezing means for exerting squeezing forces on said body part.

10. In apparatus as defined in claim 9, said support means comprising three parallel adjacent bar members with the intermediate one of said members being stationary and with the outside members being movable downwardly, said squeezing means comprising a tensioned element extending from one of said outside members to the other over said body part.

11. In a method for measuring a subject's psychological suggestibility component, the steps of supporting a part of a subject's body, applying a certain physical stimulus to said body part such as to produce a physical reaction in proportion to the subject's psychological suggestibility component, and detecting the presence of said component by detecting when said physical reaction exceeds a certain threshold value.

12. In a method as defined in claim 11, applying said certain physical stimulus by supporting the body part on a plurality of members and lowering one of the members to suggest lowering of the body part and to evoke raising of the body part by the subject in proportion to the subject's psychological suggestibility component, and detecting the existence of said component by sensing a certain raising movement of said body part.

13. In a method as defined in claim 12, applying a slightly uncomfortable pressure against an upper surface of said body part and also applying squeezing forces to said body part while simultaneously lowering said one of the members.

14. In a method as defined in claim 11, applying said certain physical stimulus by applying a slightly uncomfortable pressure against a surface of said body part.

15. In a method as defined in claim 11, applying said certain physical stimulus by applying squeezing forces to said body part.

* * * * *